United States Patent
Martin, Jr. et al.

[11] Patent Number: 5,992,413
[45] Date of Patent: Nov. 30, 1999

[54] HEAT AND MOISTURE EXCHANGER AND GENERATOR

[75] Inventors: Robert M. Martin, Jr., Hardy, Va.; Elbert J. Smith, Jr., Crafton, Md.

[73] Assignee: Enternet Medical, Inc., Las Vegas, Nev.

[21] Appl. No.: 08/997,767

[22] Filed: Dec. 24, 1997

[51] Int. Cl.$^6$ ................................................. A62B 18/08
[52] U.S. Cl. ............................... 128/201.13; 128/202.26; 128/204.17; 128/205.28
[58] Field of Search .................. 128/200.24, 201.13, 128/202.26, 204.17, 205.27, 205.28, 207.14

[56] References Cited

U.S. PATENT DOCUMENTS

| | | |
|---|---|---|
| 2,912,982 | 11/1959 | Barsky ................................ 128/207.14 |
| 3,721,238 | 3/1973 | Wise et al. ......................... 128/205.28 |
| 3,747,598 | 7/1973 | Cowans . |
| 3,782,081 | 1/1974 | Munters . |
| 3,932,153 | 1/1976 | Byrns . |
| 4,036,616 | 7/1977 | Byrns . |
| 4,040,804 | 8/1977 | Harrison . |
| 4,063,913 | 12/1977 | Kippel et al. . |
| 4,090,513 | 5/1978 | Togawa . |
| 4,108,172 | 8/1978 | Moore, Jr. . |
| 4,133,656 | 1/1979 | Kippel et al. . |
| 4,148,732 | 4/1979 | Burrow et al. . |
| 4,168,706 | 9/1979 | Lovell . |
| 4,171,962 | 10/1979 | Kippel et al. . |
| 4,172,709 | 10/1979 | Kippel et al. . |
| 4,181,511 | 1/1980 | Kippel et al. . |
| 4,181,512 | 1/1980 | Kippel et al. . |
| 4,200,094 | 4/1980 | Gedeon et al. . |
| 4,224,939 | 9/1980 | Lang . |
| 4,297,117 | 10/1981 | Holter et al. . |
| 4,360,018 | 11/1982 | Choksi ................................ 128/205.12 |
| 4,367,734 | 1/1983 | Benthin . |
| 4,458,679 | 7/1984 | Ward . |
| 4,516,573 | 5/1985 | Gedeon . |
| 4,597,917 | 7/1986 | Lunsford . |
| 4,707,167 | 11/1987 | Saito et al. . |
| 4,771,770 | 9/1988 | Artemenko et al. . |
| 4,790,327 | 12/1988 | Depotis ................................ 128/719 |
| 4,829,997 | 5/1989 | Douwens et al. . |
| 5,016,628 | 5/1991 | Lambert . |
| 5,022,394 | 6/1991 | Chmielinski . |
| 5,035,236 | 7/1991 | Kanegaonkar . |
| 5,038,767 | 8/1991 | Jumpertz . |
| 5,109,471 | 4/1992 | Lang . |
| 5,143,060 | 9/1992 | Smith ................................ 128/205.18 |
| 5,172,686 | 12/1992 | Anthony . |
| 5,195,527 | 3/1993 | Hicks . |

(List continued on next page.)

FOREIGN PATENT DOCUMENTS

| | | | |
|---|---|---|---|
| 0533644A2 | 9/1991 | European Pat. Off. .......... | 128/201.13 |
| 1910496 | 9/1970 | France .............................. | 128/205.28 |
| 1328354 | 8/1973 | United Kingdom .............. | 128/205.28 |
| 2053695 | 7/1979 | United Kingdom .............. | 128/204.17 |
| 2167307 | 11/1984 | United Kingdom .............. | 128/202.26 |
| WO 89/04684 | 6/1989 | WIPO .............................. | 128/204.17 |
| WO 92/20404 | 11/1992 | WIPO .............................. | 128/205.28 |

*Primary Examiner*—John G. Weiss
*Assistant Examiner*—Joseph F. Weiss, Jr.
*Attorney, Agent, or Firm*—Stout, Uxa, Buyan & Mullins, LLP; Frank J. Uxa

[57] ABSTRACT

Apparatus for heating and humidifying respiratory gases comprise a housing, a gas permeable member and generating material. The housing includes an inlet adapted for connection to a tracheal tube and an outlet adapted for connection to a tube for passing respiratory gases. The inlet and the outlet are positioned so that respiratory gases passing through the housing pass therebetween. The gas permeable member, for example, a conventional heat and moisture exchanger member, is positioned in the housing between the inlet and the outlet and is adapted to exchange heat and moisture with respiratory gases passing through the housing. The generating material, for example, a carbon dioxide absorbing component, is located in the housing between the inlet and the outlet and is adapted to generate water, and preferably heat, available to humidify, and preferably heat, respiratory gases passing through the housing.

24 Claims, 2 Drawing Sheets

U.S. PATENT DOCUMENTS

| | | | |
|---|---|---|---|
| 5,213,096 | 5/1993 | Kihlberg et al. . | |
| 5,228,435 | 7/1993 | Smith | 128/205.28 |
| 5,230,727 | 7/1993 | Pound et al. . | |
| 5,255,674 | 10/1993 | Oftedal et al. . | |
| 5,320,096 | 6/1994 | Hans . | |
| 5,337,739 | 8/1994 | Lehman . | |
| 5,360,002 | 11/1994 | Smith | 128/205.28 |
| 5,383,447 | 1/1995 | Lang . | |
| 5,386,825 | 2/1995 | Bates . | |
| 5,390,668 | 2/1995 | Lehman . | |
| 5,435,298 | 7/1995 | Anthony . | |
| 5,435,299 | 7/1995 | Langman . | |
| 5,460,172 | 10/1995 | Eckerbom et al. . | |
| 5,462,048 | 10/1995 | Lambert et al. . | |
| 5,468,451 | 11/1995 | Gedeon . | |
| 5,482,031 | 1/1996 | Lambert . | |
| 5,487,382 | 1/1996 | Bezicot . | |
| 5,505,768 | 4/1996 | Altadonna . | |
| 5,546,930 | 8/1996 | Wikefeldt . | |
| 5,558,088 | 9/1996 | Smith | 128/205.28 |
| 5,570,684 | 11/1996 | Behr . | |
| 5,577,494 | 11/1996 | Kuypers et al. . | |
| 5,590,644 | 1/1997 | Rosenkoetter . | |
| 5,647,344 | 7/1997 | Turnbull . | |
| 5,906,201 | 5/1999 | Nilson | 128/203.16 |

HEAT AND MOISTURE EXCHANGER AND GENERATOR

BACKGROUND OF THE INVENTION

The present invention relates to apparatus useful to exchange and generate heat and moisture in respiratory gas applications. More particularly, the invention relates to apparatus for heating and humidifying respiratory gases which exchange heat and moisture with respiratory gases and generate heat and moisture available to heat and humidify respiratory gases.

During surgery and other medical procedures, a patient is frequently connected to an anesthesia machine or ventilator to provide respiratory gases to the patient. The respiratory gases passed to the patient are advantageously heated and humidified so that the gases entering the patient are of a suitable temperature and humidity so as not to adversely impact the patient. Heat and moisture exchangers (HMEs) are often used to provide heat and humidity to the respiratory gases entering the patient. Typically, these HMEs are located so that respiratory gases from the patient pass through a tracheal tube into the HME, which is often a fibrous or other gas permeable material, which accumulates or collects heat and moisture from the exhaled gases. During the inhaling of respiratory gases, for example, from an anesthesia machine, the HME provides both heat and moisture to these respiratory gases prior to the gases entering the patient. Over a period of time, the HME is effective to maintain a certain level of temperature and humidity in the respiratory gases entering the patient.

Such HMEs do, however, have certain drawbacks. For example, during the initial or start up phase of the operation of a HME member, the amount of heat and moisture being exchanged out of the HME member to the respiratory gases being passed back to the patient is relatively low, for example, because the HME member is at a reduced temperature and a reduced moisture content. This "start up" problem can adversely affect the patient. One approach to overcoming at least a portion of this problem is to provide the HME member with a hygroscopic component, for example, calcium chloride and the like components, which is effective to generate a limited amount of heat as the exhaled gases leaving the patient pass through the HME member. This provides a "quick warm up" HME member and at least provides a heated respiratory gas stream to the patient relatively quickly. However, the degree of humidification of the respiratory gases being passed to the patient still is relatively low during the first portion of the HME member operation, in part because of the water held by the hygroscopic component.

In addition, the inefficiencies of the typical HME member are such that a certain portion of the heat and moisture collected by the HME is lost, for example, to the environment and otherwise, rather than being passed back to the patient by exchange with respiratory gases. The degree of heating and/or humidification of the respiratory gases varies, and in particular decreases, over time which can adversely impact the patient.

It would be advantageous to provide a system by which respiratory gases can be effectively, reliably, straightforwardly and controllably provided with both heat and moisture so that the comfort and safety of a patient undergoing surgery and/or other medical treatment is enhanced.

SUMMARY OF THE INVENTION

New apparatus for heating and humidifying respiratory gases have been discovered. Such apparatus provide for exchanging heat and moisture with respiratory gases exhaled by the patient and providing heat and moisture to the respiratory gases being inhaled by the patient. In addition, and importantly, the present apparatus provide for very effective, reliable and controlled generation of moisture, and preferably heat, available to humidify, and preferably heat, respiratory gases passing to the patient. Thus, the combination of heat and moisture exchange and moisture, and preferably heat, generation provides very effectively for respiratory gases passed to a patient which are effectively heated and humidified. Moreover, the "start up" problem described above is reduced in severity, and even substantially eliminated, because of the generation feature of the present apparatus. Still further, the present apparatus are straightforward in construction, easy to manufacture and use, for example, requiring operation of no electrical or electronic assemblies, and can be specifically configured to provide the desired, preferably controlled, amounts of moisture and heat to the respiratory gases passing to the patient.

In one broad aspect of the present invention, apparatus for heating and humidifying respiratory gases are provided and comprise a housing, a gas permeable member and a generating material. The housing has an inlet for passing respiratory gases to and from the housing, preferably adapted for connection to a tracheal tube device, for example, positioned at least partially in a human patient, and an outlet, spaced apart from the inlet, adapted for connection to a tube for passing respiratory gases to and from the housing. As used herein, the term "tracheal tube device" means a tracheal tube, face mask, nasal tube or other element or assembly adapted to be in contact with or in close proximity to a patient and to be effective in passing respiratory gases to and from the patient, for example, the lungs of a patient. The inlet and the outlet are positioned so that respiratory gases, that is both gases which are inhaled by a patient and exhaled by the patient, which pass through the housing are passed between the inlet and the outlet. The gas permeable member is positioned in the housing between the inlet and the outlet and is adapted to exchange heat and moisture with respiratory gases passing through the housing. This gas permeable member can be of any suitable, for example, conventional, configuration, that is a conventional heat and moisture exchanger member useful in current HMEs. The generating material noted above is located in the housing between the inlet and the outlet and is adapted to generate water, and preferably heat, available to humidify, and preferably heat, respiratory gases passing through the housing.

The generating material noted above preferably is entirely contained within the housing so that the moisture, and preferably heat, generation occurs entirely within the housing. Thus, preferably no external water and/or heat source or other components, for example, electric wires, water tubes and the like, which extend outside the housing are included. The present water, and preferably heat, generating material is very effective in providing for a rapid increase in the humidity, and preferably, temperature of respiratory gases being passed to the patient. This feature reduces, and even substantially eliminates, the "start up" problem with conventional HMEs discussed above.

The generating material preferably interacts with carbon dioxide in respiratory gases passing through the housing to generate water available to humidify respiratory gases passing through the housing, and more preferably heat available to heat respiratory gases passing through the housing. The generating material more preferably absorbs carbon dioxide in respiratory gases passing through the housing in generating water, and preferably heat.

The generating material, in one embodiment, is a carbon dioxide absorbing material which can be selected from a suitable such material, for example, any one of a number of such materials which are commercially available. One such carbon dioxide absorbing material is produced by Dewey and Almy Chemical Division of W. R. Grace & Co. and is sold under the trademark "SODA-SORB". Generally this material includes active ingredients of sodium hydroxide and hydrated lime.

Without wishing to limit the invention to any particular theory of operation, it is believed that the generating material is effective to neutralize carbon dioxide with resultant production of heat and water. Using one particularly useful carbon dioxide absorbing generating material, such neutralization is believed to proceed as follows:

$$CO_2 + H_2O \leftrightharpoons H_2CO_3 \quad (i)$$

$$2H_2CO_3 + 2NA^+2 + OH^- + 2K + 2OH^- \leftrightharpoons 2NA^+ + CO_3 + 2K^+ + CO_3 + 4H_2O \quad (ii)$$

$$CA(OH)_2 + H_2O \leftrightharpoons CA^{++} + 2OH^- + H_2O \quad (iii)$$

$$2CA^{++} + 2OH^- + 2NA^+ + CO_3 + 2K^+ + CO_3 \leftrightharpoons 2CACO_3 + 2NA^+ + 2OH^- + 2K^+ + 2OH^- \quad (iv)$$

In (i) the $CO_2$ dissolves at a rate governed by a number of physical chemical factors. The rate is not proportional to the partial pressure of the $CO_2$ which is in contact with the film of moisture coating the soda lime granules, but greater—because some of the $CO_2$ combines chemically with the water to form carbonic acid. The rate is directly proportional to the rate of removal of dissolved $CO_2$, or carbonic acid, from solution, by reaction with hydroxyl ion (reaction ii). Thus, the rapidity of removal of dissolved $CO_2$ is directly related to the availability of hydroxy ions. Since the reaction between H+ and OH− is instantaneous, forming water, reaction (iii) and (iv) must supply additional hydroxyl ions to keep the absorption of $CO_2$ progressing. The latter two reactions are therefore rate limiting.

In a very useful embodiment, the amount of generating material present is effective to generate only a portion, more preferably a minor portion (that is, no more than about 50%), of the water to humidify respiratory gases passing through the housing. In particular, the amount of generating material present in the housing is effective to generate at least about 5%, more preferably at least about 10%, and still more preferably at least about 15% of the water to humidify respiratory gases passing through the housing. On the other hand, the amount of generating material present in the housing preferably is effective to generate no more than about 50% of the moisture of the water to humidify respiratory gases passing through the housing. Having excessively large amounts generating material present in the housing can result in the respiratory gases passing to the patient having a temperature which is excessively high relative to the requirements of the patient. Therefore, it is preferred that only relatively reduced amounts of water and heat, as described herein, be generated by the generating material. In the event carbon dioxide absorbing material is used as the generating material, the present apparatus preferably initially includes about 10 or about 20 grams to about 40 or about 60 or about 80 grams, more preferably about 20 grams to about 30 or about 40 grams of such material, particularly when the patient in question is an adult human being. The amount of generating material used when the patient is a human infant or a premature human infant may be somewhat less because of the very small lung tidal volumes, for example, about 10 cc or less, involved.

This controlled or limited amount of water and heat generation makes it important to provide not only the generating material but also the gas permeable member, e.g., a conventional HME member, which acts in combination with the generating material to provide the desired, preferably controlled and acceptable, degree of humidification and heating to the respiratory gases being passed to the patient.

Because the generating material preferably interacts with carbon dioxide in the respiratory gases to generate the water, and preferably heat, the amount of carbon dioxide being exhaled by the patient provides a suitable control as to the amount of water, and preferably heat, generated by the generating material. Thus, increased respiration by the patient, which results in increased production of carbon dioxide, leads to increased water, and preferably heat, generation, which is useful in humidifying and heating the increased amounts of respiratory gases required by the patient. With the generating material generating water, and preferably heat, because of an interaction with carbon dioxide, the patient and his/her respiratory needs, in effect, control the amount of water, and preferably heat, being generated in the present apparatus.

The generating material preferably is positioned in the housing adjacent the gas permeable member. In a very useful embodiment, the generating material is located nearer to the inlet than is the gas permeable member. Thus, exhaled gases from the patient preferably come in contact with the generating material before being passed to the gas permeable membrane. This arrangement is effective to provide that at least a portion of the water and heat generated by the generating material is accumulated or collected by the gas permeable member and is available for use in humidifying and heating the respiratory gases being passed to the patient.

The generating material in the housing is often of such a character that after a period of time in service (in the present apparatus) a deactivated material is formed. For example, the generating material may include one or more active components which are consumed and/or otherwise rendered ineffective to generate water, and preferably heat, after time in service in the present apparatus. The deactivated material is derived from the generating material and preferably includes such consumed and/or otherwise ineffective components. In any event, the deactivated material has substantially no ability to generate water or heat available to humidify or heat respiratory gases passing through the housing. However, it has been found that the present apparatus including the deactivated material in place of the generating material has a greater ability to humidify and heat respiratory gases passing through the housing relative to an identical apparatus without either the generating material or the deactivated material.

Without wishing to limit the invention to any particular theory of operation, it is believed that the deactivated material, even though it is ineffective to generate water and heat, is at least to some extent effective to transfer, e.g., store or collect and release, moisture and heat with the respiratory gases passing through the housing. The apparatus with the deactivated material in place of the generating material has increased moisture/heat transfer capacity relative to an identical apparatus without either the generating material or the deactivated material. The present apparatus provide substantial benefits even though the generating material is rendered ineffective and forms the deactivated material.

In a useful embodiment, the housing has a longitudinal axis and the gas permeable member and the generating material are positioned substantially perpendicular to the longitudinal axis of the housing. The gas permeable member and the generating material may be positioned substantially perpendicular to the general direction of flow of respiratory gases passing through the housing.

The inlet and the outlet of the housing can be aligned or may be non-aligned. The housing can have any suitable configuration effective to meet the requirements of the application in which the apparatus is to be used.

The gas permeable member and the generating material may be positioned at an angle other than 90° relative to the longitudinal axis of the housing. This feature allows for a relatively compact and/or flat structure of the housing while, at the same time, providing substantially the same amount of gas permeable member and generating material relative to a system of which these components are positioned substantially perpendicular to the general direction of flow of respiratory gases through the housing.

As noted above, the gas permeable member may be of any suitable configuration and composition. In particular, the gas permeable member may include fibers, fibrous materials and the like, many of which are conventionally used in HMEs. Moreover, the present gas permeable member may include an effective amount of a hygroscopic component which is effective to provide a controlled amount of heat to the respiratory gases passing through the housing during the early portion or "start up" portion of the operation of the present apparatus.

In another aspect, the present apparatus further comprises a filter element located in the housing between the inlet and the outlet and adapted to filter respiratory gases passing through the housing. Such filter element is useful to remove contaminants, for example, liquid particles, microbes and/or other contaminating materials, from the respiratory gases, in particular, being passed or exhaled by the patient. The filter element may have antimicrobial activity to at least reduce the number of microorganisms being passed through the housing. Preferably, the filter element is positioned in the housing adjacent the generating material. More preferably, the generating material is positioned between the gas permeable member and the filter element. In order to enhance the effectiveness of the filter element it preferably is located closer to the inlet than is the gas permeable member. Also, as noted previously, the generating material preferably is located closer to the inlet than is the gas permeable member. Thus, starting with the inlet, it is preferred that the exhaled gases from the patient contact, in sequence, the filter element, the generating material and the gas permeable member.

Each individual feature and each combination of two or more features described herein are included within the scope of the present invention provided that the features included in the combination are not mutually inconsistent.

These and other aspects and advantages of the present invention are set forth in the following detailed description and claims, particularly when considered in conjunction with the accompanying drawings in which like parts bear like reference numerals.

DETAILED DESCRIPTION OF THE DRAWINGS

Figure 1:
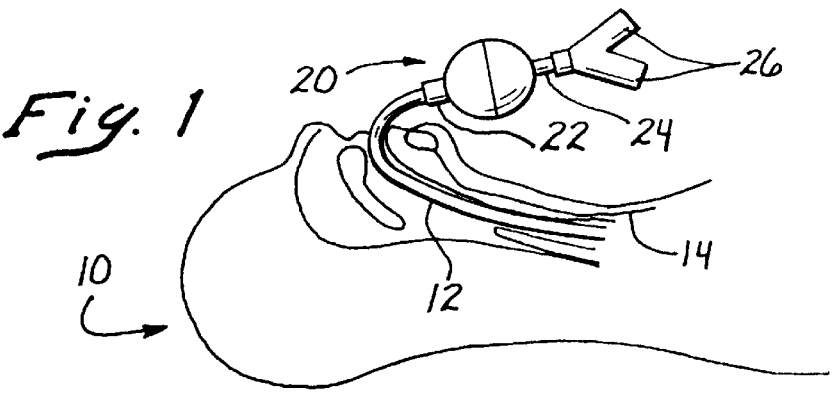
FIG. 1 is a schematic illustration showing an embodiment of the present invention being used for moisture and heat exchange and generation with respect to respiration gases passed to and from a patient.

FIG. 1 shows a patient 10 being treated so as to provide respiratory gases to the patient. A tracheal tube 12 is inserted in the trachea 14 of the patient 10. The tracheal tube 12 is connected to the heat and moisture exchanger generator (HMEG) apparatus, shown generally at 20, specially to the inlet 22 of the apparatus. The outlet 24 of apparatus 20 is joined or connected to one or more hoses 26 which communicate with an anesthesia machine or a ventilator. In this arrangement, the patient 10 is provided with respiratory gases from the anesthesia machine or ventilator through hoses 26. Such gases pass into the apparatus 20, through tracheal tube 12 into the trachea of the patient 10. Exhaled respiratory gases pass from the trachea 14 through the tracheal tube 12 and the apparatus 20 and into the hoses 26. This cycle is repeated each time patient 10 inhales and exhales respiratory gases.

Figure 2:
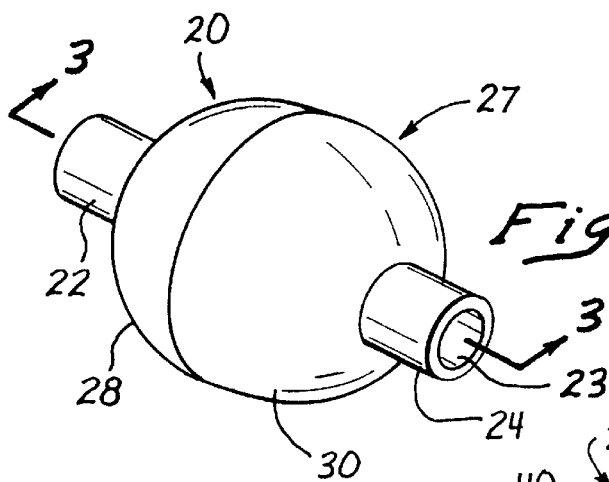
FIG. 2 is a front side view, in perspective, of the embodiment of the present apparatus shown in FIG. 1.
Figure 3:
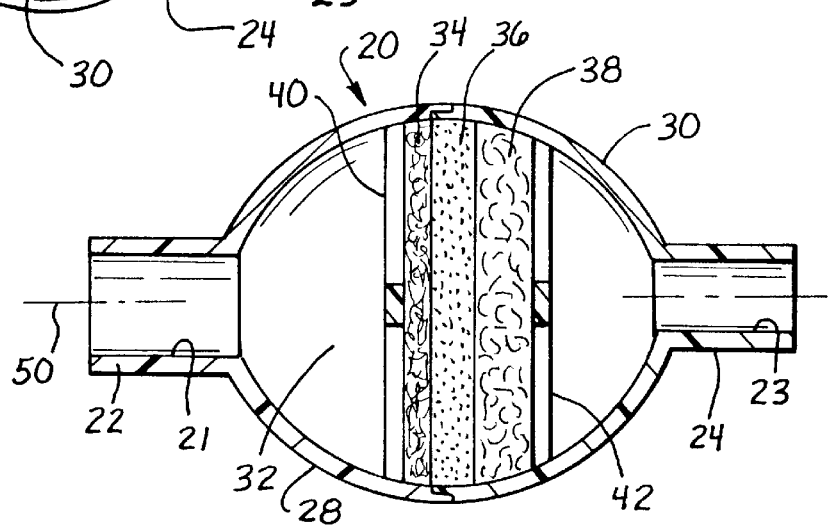
FIG. 3 is a cross-sectional view taken generally along line 3—3 of FIG. 2.

As shown in FIGS. 2 and 3, HMEG apparatus 20 includes a housing 27 including a first housing section 28, a second housing section 30 which are joined together in an overlapping interference fit. First and second housing sections 28 and 30 can be bonded together to provide for total disposability, for example, when the apparatus is to be used for a relatively short period of time. When housing sections 28 and 30 are joined together, a hollow chamber 32 is formed by this coupled structure. Located within the chamber 32 and extending substantially across the entire cross-section of the chamber are an antimicrobial filter element 34, a quantity of particulate carbon dioxide absorbing material 36 and a gas permeable fibrous member 38. First housing section 28 includes a first support member 40, in the form of a cross. Similarly, second housing section 30 includes a second support member 42 in the form of a cross. First and second support members 40 and 42 are positioned so that they provide support for the filter element 34, carbon dioxide absorbing material 36 and fibrous member 38 so that these components remain in the desired location. The support members 40 and 42 are sufficiently strong to provide the desired support while, at the same time, being sufficiently thin to minimize the degree to which these support members block the flow of respiratory gases through apparatus 20.

Respiratory gases from patient 10 pass through inlet passage 21, defined by inlet 22, into chamber 32. Inlet 22 is defined by first housing section 28. Such respiratory gases pass through filter element 34, carbon dioxide absorbing material 36 and fibrous member 38 before exiting through outlet passage 23, defined by outlet 24. Outlet 24 is defined by second housing section 30. When respiratory gases are to be inhaled by patient 10, such gases pass into apparatus 20 through outlet passage 23 into chamber 32, across fibrous member 38, carbon dioxide absorbing material 36 and filter element 34. This respiratory gas to be inhaled is passed through inlet passage 21 into tracheal tube 12 and into the trachea 14 of the patient 10.

The inlet 22 and outlet 24 are both aligned with the longitudinal axis 50 of apparatus 20. The filter element 34, carbon dioxide absorbing material 36 and fibrous member 38 are all positioned substantially perpendicular to the longitudinal axis 50. Thus, the filter element 34, carbon dioxide absorbing material 36 and fibrous member 38 are all positioned substantially perpendicular to the general direction of flow between the inlet passage 21 and the outlet passage 23.

The filter element 34 may be of any suitable configuration effective to remove contaminants from the respiratory gases passing therethrough. The filter element 34 should be sufficiently gas permeable so that the respiratory gases passing therethrough result in a relatively reduced, or even minimal pressure differential. The filter element 34 may be chosen from filter material used in conventional respiratory filters or heat and moisture exchangers for respiratory gases, many of which are known and commercially available. The filter element 34 may have antimicrobial activity.

The fibrous member 38 is selected to provide for both heat and moisture exchange with gases passing through the housing 27. The fibrous member 38 may be chosen from any suitable material which is effective as a heat and moisture exchanging material and has gas permeability. Examples of useful materials from which fibrous member 38 can be chosen include such materials which are conventionally used in heat and moisture exchangers for respiratory gases, many of which are well known and commercially available.

The carbon dioxide absorbing material 36, which is located between and adjacent the filter element 34 and fibrous member 38, is effective to generate both water and heat in response to an interaction with carbon dioxide, for example, the absorption of and subsequent reaction with carbon dioxide, in the respiratory gas which comes in contact with the carbon dioxide absorbing material. The carbon dioxide absorbing material 36 is preferably in the form of particles which are effective to absorb, or otherwise interact with, carbon dioxide in the respiratory gases. The carbon dioxide absorbing material 36 preferably is sufficiently gas permeable so that respiratory gases passing therethrough result in a relatively reduced, or even in a minimal pressure differential. Although any suitable component or combinations of components may be used in carbon dioxide absorbing material 36 to generate moisture and heat, it is preferred that the carbon dioxide absorbing material be that sold by W. R. Grace under the trademark "SODA SORB".

The HMEG apparatus 20 functions as follows. The HMEG apparatus 20 is connected to the respiratory assist system of patient 10 as described above. As the patient exhales respiratory gases, such gases pass through inlet passage 21 into chamber 32. These exhaled gases pass through filter element 34 and are at least to some extent purified in that contaminants are removed and/or destroyed. This exhaled respiratory gas includes carbon dioxide at least a portion of which interacts with the carbon dioxide absorbing material 36 as the exhaled respiratory gases pass therethrough. This results in the generation of heat and moisture which passes into fibrous member 38, along with the heat and moisture originally present in the respiratory gases being exhaled by patient 10. This heat and moisture is collected by fibrous member 38 as the exhaled respiratory gases pass therethrough. The exhaled respiratory gases pass out of apparatus 20 through outlet passage 23. During the time patient 10 is inhaling gases, for example, from tubes 26, such respiratory gases to be inhaled are passed into HMEG apparatus 20 through outlet passage 23. The to be inhaled gases pass through the fibrous member 38 where heat and moisture from the fibrous member are transferred to the respiratory gases to be inhaled. Additional heat and moisture is released to the respiratory gases to be inhaled as the gases pass through the carbon dioxide absorbing material 36 to provide the desired amount of heat and moisture to such gases. Finally, the respiratory gases to be inhaled passes through the filter element 34 and out of apparatus 20 through inlet passage 21 into the tracheal tube 12 and trachea 14 of the patient 10.

This exhale/inhale cycle is continued with the result that the patient 10 is provided with respiratory gases which have the desired degree of heat and humidity so that the patient is not detrimentally affected by respiratory gases which are too dry or too cold.

The amount of carbon dioxide absorbing material is sufficient to provide about 20 percent to about 40 percent, more preferably about 25 percent, of the moisture to the respiratory gases to be inhaled by patient 10. Providing more than about 50 percent of the moisture to the respiratory gases to be inhaled can result in an excessive increase in the temperature of the inhaled gases which can have a detrimental effect on the patient 10.

Thus, it is important that both the carbon dioxide absorbing material 36 and the fibrous member 38 be used together, more preferably with the carbon dioxide absorbing material on the inlet side of the fibrous member, to provide a portion, for example, a minor portion, of the moisture, and preferably heat, to the respiratory gases inhaled by patient 10.

Over a period of time, the active material in carbon dioxide absorbing material 36 is consumed. After a substantial amount of this carbon dioxide absorbing component material 36 has been consumed, the HMEG apparatus 20 can be replaced by a new HMEG apparatus 20 simply by removing the used apparatus 20 and providing in its place a new apparatus 20 with a new carbon dioxide absorbing material 36.

Alternately, even after the carbon dioxide absorbing material has lost its effectiveness to generate moisture and heat, the HMEG apparatus 20 can continue in service, at least for as extended period of time, and provide enhanced levels of moisture and heat to the respiratory gases to be inhaled by patient 10. This is so because it has been found that apparatus 20, even with a deactivated carbon dioxide absorbing material 36, is effective to provide increased levels of moisture and heat to respiratory gases to be inhaled relative to an identically structured apparatus with no carbon dioxide absorbing material 36 or no deactivated carbon dioxide absorbing material.

Figure 4:
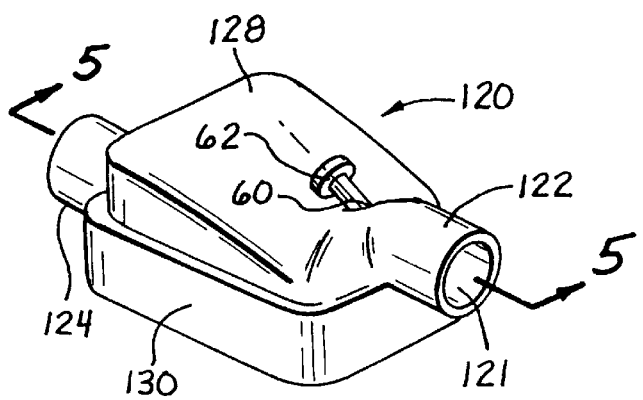
FIG. 4 is a top side view, in perspective, of another embodiment of the apparatus of the present invention.
Figure 5:
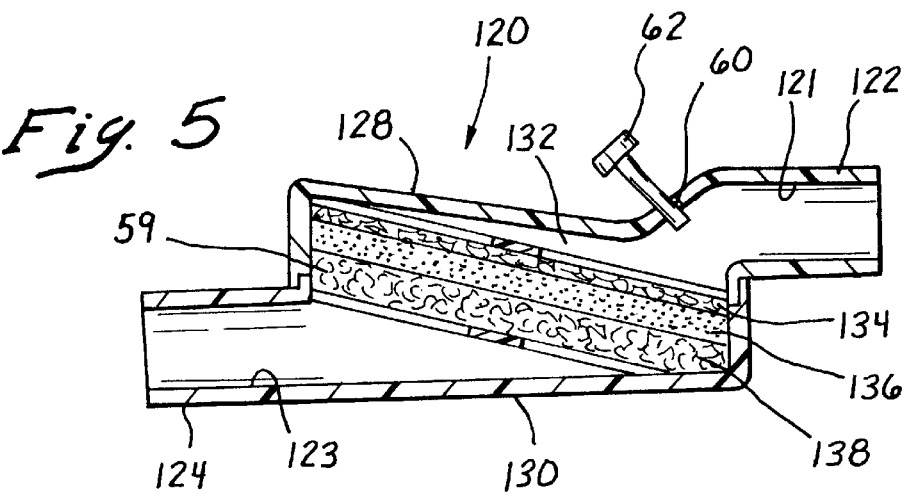
FIG. 5 is a cross-sectional view taken generally along line 5—5 of FIG. 4.

FIGS. 4 and 5 illustrate another embodiment of the present apparatus. Except as expressly described herein, this embodiment, shown generally at 120, is structured and functions similarly to apparatus 20. Components of HMEG apparatus 120 which correspond to components of HMEG apparatus 20 are identified by the same reference numeral increased by 100.

The primary differences between apparatus 120 and apparatus 20 involve the relationship between inlet 122 and outlet 124, and the positioning of filter element 134, carbon dioxide absorbing component 136 and fibrous member 138.

Specifically, the inlet 122 of apparatus 120 is not aligned or coaxial with outlet 124. Inlet 22 is coaxial with outlet 24. In addition, the configuration of first housing section 128 and second housing section 130 is such that the chamber 132 defined thereby is relatively flat, as compared to the relatively round, or even spherical, configuration of chamber 32 of apparatus 20.

In addition, the orientation of filter element 134, carbon dioxide absorbing material 136 and fibrous member 138 are at an angle other than 90 degrees relative to the general direction of gas flowing through the inlet passage 121 and outlet passage 123. In other words, the orientation of filter element 134, carbon dioxide absorbing component material 136 and fibrous component 138 is at an angle other than 90 degrees relative to the general direction of flow entering and exiting apparatus 120.

The configuration of apparatus 120 is more compact relative to apparatus 20. Thus, apparatus 120 can be used in situations where space is a premium. Also, apparatus 120 has a reduced amount of air or dead space within chamber 132 which is beneficial in reducing the losses of heat and moisture to the environment and provides for more effective passage of respiratory gases into and out of the patient during each exhale/inhale cycle.

In addition, apparatus 120 includes a hygroscopic component 59, such as calcium chloride, lithium chloride and the like, secured to, for example, coated on, fibrous member 138. Hygroscopic component 59 is effective, particularly during the initial use of apparatus 120, to provide heat, for example, by the exothermic absorption of water, to the respiratory gases to be inhaled by the patient. Hygroscopic component 59 can be included in all of the embodiments of the present invention, for example, the embodiments described herein.

One further distinction between apparatus 120 and apparatus 20 has to do with the presence of carbon dioxide sampling port 60 which is normally closed or covered by plug 62. Sampling port 60, on the inlet side of apparatus 120, can be used, when desired, to monitor the quality of the respiratory gases being passed to and exhaled by the patient. Thus, when a sample is desired, plug 62 can be removed from sampling port 60 and a sensor inserted to monitor carbon dioxide concentration of the gas at that point of apparatus 120. It should be noted that such a sampling arrangement can be provided to apparatus 20, as well as the other embodiments of the present invention. The sampling should be taken, if at all, during patient exhalation and on the inlet or patient side of the carbon dioxide absorbing material 136 so that the concentration of carbon dioxide in the respiratory gases is not influenced by the carbon dioxide absorbing material.

Figure 6:
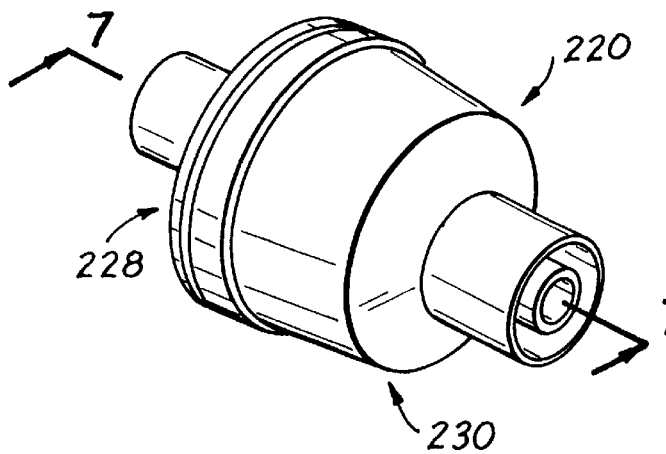
FIG. 6 is a front side view, in perspective of an additional embodiment of the apparatus of the present invention.
Figure 7:
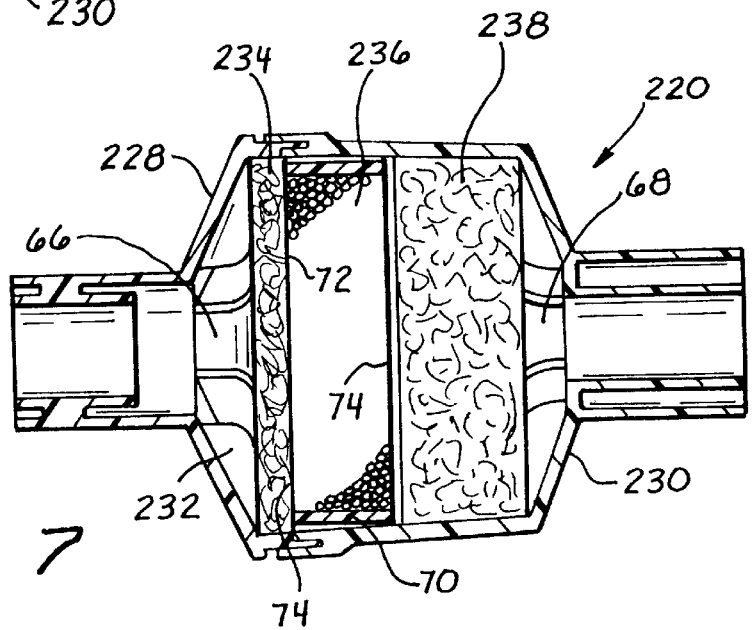
FIG. 7 is a cross-sectional view taken generally along line 7—7 of FIG. 6.

FIGS. 6 and 7 illustrate an additional embodiment of the present apparatus, shown generally at 220. Unless expressly described, HMEG apparatus 220 is structured and functions similarly to apparatus 20. Components of apparatus 220 which correspond to components of apparatus 20 are identified by the same reference numeral increased by 200.

The primary differences between the HMEG apparatus 220 and the apparatus 220 relate to the structure of the housing components and the structure of the compartment holding the carbon dioxide absorbing material.

Specifically, first housing section 228 includes a series of first support ribs 66 which extend inwardly into chamber 232 and are effective to provide support at the inlet side to filter element 234, carbon dioxide absorbing material 236 and fibrous member 238. Second housing section 230 includes a series of second support ribs 68 which extend inwardly into chamber 232 and provide support for the outlet side of fibrous member 238, carbon dioxide absorbing material 236 and filter element 234. The combination of first support ribs 66 and second support ribs 68 act to maintain filter element 234, carbon dioxide absorbing material 236 and fibrous member 238 in place within chamber 232. First and second support ribs 66 and 68 replace the support members 40 and 42.

Carbon dioxide absorbing material 236 is encased in a container including a polymeric ring 70 surrounding the sides of the carbon dioxide supporting material. The container also includes gauze like end members 72 and 74 which keep carbon dioxide absorbing material 236 in place while, at the same time, allowing respiratory gases to pass through the carbon dioxide absorbing material with a relatively minimal pressure differential. Using such a confined carbon dioxide material 236 allows the user, if desired, to replace the spent carbon dioxide absorbing material 236 with a new similarly structured container of active carbon dioxide absorbing material. This feature reduces the cost of using apparatus 220 and promotes the desired conditioning of respiratory gases to the patient.

One additional feature of apparatus 220 is the reduced amount of air or dead space included within chamber 232, resulting in benefits similar to those described with regard to apparatus 110.

While the invention has been described with respect to various specific examples and embodiments, it is to be understood that the invention is not limited thereto and that it can be variously practiced within the scope of the following claims.

What is claimed is:

1. An apparatus for heating and humidifying respiratory gases comprising:

a housing having a first port adapted for passing respiratory gases between the housing and a patient and a second port adapted for connection to a tube for passing respiratory gases to and from the housing, the first port and the second port being positioned so that respiratory gases passing to and from the housing through the housing pass therebetween;

a gas permeable member positioned in the housing between the first port and the second port and adapted to exchange heat and moisture with respiratory gases passing through the housing; and a generating material located in the housing between the first port and the second port and adapted to generate water available to humidify respiratory gases passing through the housing.

2. The apparatus of claim 1 wherein the generating material is further adapted to generate heat available to heat respiratory gases passing through the housing and the first port is further adapted for connection to a tracheal tube device.

3. The apparatus of claim 1 wherein the generating material interacts with carbon dioxide in respiratory gases passing through the housing to generate water available to humidify respiratory gases passing through the housing.

4. The apparatus of claim 2 wherein the generating material interacts with carbon dioxide in respiratory gases passing through the housing to generate heat available to heat respiratory gases passing through the housing.

5. The apparatus of claim 3 wherein the generating material absorbs carbon dioxide in respiratory gases passing through the housing to generate water available to humidify respiratory gases passing through the housing.

6. The apparatus of claim 4 wherein the generating material absorbs carbon dioxide in respiratory gases passing through the housing to generate heat available to heat respiratory gases passing through the housing.

7. The apparatus of claim 1 wherein the generating material is present in an amount effective to generate at least about 10% of the water to humidify respiratory gases passing through the housing.

8. The apparatus of claim 1 wherein the generating material is present in an amount effective to generate no more than about 50% of the water to humidify respiratory gases passing through the housing.

9. The apparatus of claim 1 wherein the generating material after a period of time in service forms a deactivated material which has substantially no ability to generate water or heat available to humidify or heat respiratory gases passing through the housing, the apparatus including the deactivated material in place of the generating material has a greater ability to humidify and heat respiratory gases passing through the housing relative to an identical apparatus without either the generating material or the deactivated material.

10. The apparatus of claim 1 wherein the generating material is positioned adjacent the gas permeable member.

11. The apparatus of claim 1 wherein the generating material is located closer to the first port than is the gas permeable member.

12. The apparatus of claim 1 wherein the gas permeable member and the generating material are positioned substantially perpendicular to the general direction of flow of respiratory gases passing through the housing.

13. The apparatus of claim 1 wherein the first port and the second port are not aligned.

14. The apparatus of claim 13 wherein the housing has a longitudinal axis and the gas permeable member and the generating material are positioned at an angle other than 90° relative to the longitudinal axis of the housing.

15. The apparatus of claim 1 wherein the gas permeable member comprises fibers.

16. The apparatus of claim 1 which further comprises a filter element located in the housing between the first port and the second port and adapted to filter respiratory gases passing through the housing.

17. The apparatus of claim 16 wherein the filter element is positioned adjacent the generating material.

18. The apparatus of claim 16 wherein the generating material is positioned between the gas permeable member and the filter element.

19. The apparatus of claim 16 wherein the filter element is located closer to the first port than is the gas permeable element.

20. The apparatus of claim 1 which further comprises a hygroscopic component positioned in the housing between the first port and the second port and adapted to generate heat available to heat respiratory gases passing through the housing.

21. The apparatus of claim 20 wherein the hygroscopic component is secured to the gas permeable member.

22. The apparatus of claim 1 wherein the generating material is present in an amount in a range of about 10 grams to about 80 grams.

23. An apparatus for heating and humidifying respiratory gases comprising:

a housing having a first port adapted for passing respiratory gases between the housing and a housing and a second port adapted for connection to a tube for passing respiratory gases to and from the housing, the first port and the second port being positioned so that respiratory gases passing to and from the patient through the housing passes therebetween;

a gas permeable member positioned in the housing between the first port and the second port and adapted to exchange heat and moisture with respiratory gases passing through the housing; and a material located in the housing between the first port and the second port, said material initially adapted to generate moisture and heat in order to humidify and heat respiratory gases passing through the housing, then after a period of use said material being substantially ineffective to generate moisture and heat available to humidify and heat respiratory gases passing through the housing, the apparatus with the now substantially ineffective material having a greater ability to humidify and heat respiratory gases passing through the housing relative to an identical apparatus without the substantially ineffective material.

24. The apparatus of claim 23 wherein the material is present in the form of particles.

* * * * *